(12) United States Patent
Godlieb

(10) Patent No.: US 9,007,877 B2
(45) Date of Patent: Apr. 14, 2015

(54) ILLUMINATION DEVICE WITH WAKE-UP FUNCTION

(75) Inventor: Robert Godlieb, Drachten (NL)

(73) Assignee: Koninklijke Philips N.V., Eindhoven (NL)

( * ) Notice: Subject to any disclaimer, the term of this patent is extended or adjusted under 35 U.S.C. 154(b) by 172 days.

(21) Appl. No.: 13/497,179

(22) PCT Filed: Oct. 22, 2010

(86) PCT No.: PCT/IB2010/054798
§ 371 (c)(1),
(2), (4) Date: Mar. 20, 2012

(87) PCT Pub. No.: WO2011/051869
PCT Pub. Date: May 5, 2011

(65) Prior Publication Data
US 2012/0200234 A1 Aug. 9, 2012

(30) Foreign Application Priority Data
Oct. 29, 2009 (EP) ..................................... 09174416

(51) Int. Cl.
*G04B 19/30* (2006.01)
*H05B 37/02* (2006.01)
*G04G 11/00* (2006.01)
*A61N 5/06* (2006.01)
*A61M 21/00* (2006.01)

(52) U.S. Cl.
CPC ........ *G04G 11/00* (2013.01); *A61N 2005/0663* (2013.01); *A61N 2005/0652* (2013.01); *A61M 2021/0083* (2013.01); *A61M 2021/0044* (2013.01); *A61M 21/00* (2013.01)

(58) Field of Classification Search
USPC ................. 315/149, 152, 153, 291, 294, 297; 340/6.1, 10.33, 575, 815.4; 368/67, 68, 368/72, 74, 243, 244
See application file for complete search history.

(56) References Cited

U.S. PATENT DOCUMENTS

| 5,327,331 | A | 7/1994 | Roberts |
| 7,280,439 | B1 | 10/2007 | Shaddox |
| 8,499,593 | B2* | 8/2013 | Van De Sluis et al. ......... 68/256 |
| 2003/0231495 | A1 | 12/2003 | Searfoss, III |
| 2004/0264193 | A1 | 12/2004 | Okumura |
| 2005/0128743 | A1 | 6/2005 | Chuey |
| 2008/0224024 | A1 | 9/2008 | Ashdown |
| 2010/0277316 | A1* | 11/2010 | Schlangen et al. ............ 340/540 |

(Continued)

FOREIGN PATENT DOCUMENTS

| EP | 1462711 | A1 | 9/2004 |
| GB | 2308901 | A | 7/1997 |
| JP | 2001284065 | | 10/2001 |
| JP | 2009224277 | A | 10/2009 |

(Continued)

*Primary Examiner* — Douglas W Owens
*Assistant Examiner* — Thai Pham

(57) ABSTRACT

An illumination device with wake-up and/or fall-asleep functionality is disclosed. The illumination devices comprises at least one controllable light source; a control device for controlling the light source, wherein in a STEADY mode, color and intensity of the output light are maintained constant at a steady colour value and a steady intensity value and in and a WAKE-UP mode, the intensity of the output light is gradually increased from zero to the steady intensity value and in a FALL-ASLEEP mode, the intensity of the output light is gradually decreased from the steady intensity value to zero.

8 Claims, 3 Drawing Sheets

(56) References Cited

U.S. PATENT DOCUMENTS

2010/0278016 A1* 11/2010 Sandu et al. .................. 368/10
2013/0241437 A1 9/2013 Baaijens

FOREIGN PATENT DOCUMENTS

| WO | 0136864 A2 | 5/2001 |
|----|------------|--------|
| WO | 2009090596 A1 | 7/2009 |

* cited by examiner

ILLUMINATION DEVICE WITH WAKE-UP FUNCTION

FIELD OF THE INVENTION

The present invention relates in general to an illumination device capable of producing light with variable intensity. Particularly, the present invention relates to a so-called wake-up lamp or, conversely, a so-called fall-asleep lamp.

BACKGROUND OF THE INVENTION

A wake-up lamp is a lamp comprising one or more light sources, of which the power (corresponding to light intensity) is slowly and gradually increased from zero (or a starting value close to zero) to a maximum value during a certain time period, for instance 30 minutes, and after that the power is maintained. Such a lamp is used to simulate the natural process of increasing daylight level at sunrise, which has a positive effect on people waking up. The process can also be run in reverse, so that the power (corresponding to light intensity) is slowly and gradually decreased from the maximum value to zero (or an end value close to zero), to simulate the natural process of decreasing daylight level at sunset, which has a positive effect on people going to sleep.

Wake-up lamps and fall-asleep lamps are commonly known, so a more detailed explanation is omitted here. Further, for sake of convenience, the following explanation will focus on wake-up lamps but the same explanation applies, mutatis mutandis, to fall-asleep lamps, as should be clear to a person skilled in the art.

Wake-up lamps can be implemented with different types of light sources. For instance, the light source used can be an incandescent lamp, a discharge lamp, an LED, etc. Varying the output power of a light source is typically done by varying the lamp current.

SUMMARY OF THE INVENTION

An important feature of light generated by a light source is its colour. Typically, the light colour may depend on the lamp current. For instance, in the case of an incandescent lamp, at a low lamp current the light colour is glowing red to orange (corresponding to a relatively low temperature of the lamp spiral) whereas at a high lamp current the light colour is yellow to white (corresponding to a relatively high temperature of the lamp spiral). As such, this is a positive effect since it roughly corresponds to the change in colour of the sunlight on sunrise (and, conversely, sunset). On the other hand, there are also light sources where the colour is constant, independent of the lamp current.

In the following, the said time period during which the light intensity is slowly increased or decreased will be indicated as the wake-up cycle time or the fall-asleep cycle time, respectively. Further, the light intensity outputted after completing the wake-up cycle time will be indicated as the steady state intensity, corresponding with a steady state current. Normally, the steady state current is equal to the maximum or nominal current designed for the light source(s) concerned, and hence the steady state intensity is equal to the maximum or nominal light intensity. The present invention aims to provide a user with the possibility of setting the level of the steady state intensity.

This aim could easily be achieved by just limiting the lamp current to a certain level. However, the concomitant problem is that the light colour corresponding to such a reduced steady state current differs from the bright white colour normally associated with the full completion of the wake-up cycle. This is illustrated in FIG. 1.

In the left-hand diagram, curve 1 illustrates the lamp current or light intensity (vertical axis, arbitrary units) as a function of time (horizontal axis, minutes) rising from zero to a maximum value of 300 within a wake-up cycle time of 30 minutes. The corresponding colour change is indicated by curve 2. Admittedly, it is difficult to visualize the colour in this diagram, but it is assumed that for the colour the vertical axis represents a line from red to white in a colour diagram. Further, for sake of illustration, it is assumed that the position along such a colour line is directly proportional to the light intensity.

The right-hand diagram illustrates a situation where the user has set the steady state intensity to 100, or 33% of the maximum value (curve 1') while the wake-up cycle time is maintained at 30 minutes (although this is not essential). Curve 2' indicates the corresponding colour change for the straightforward implementation where the light intensity is just limited to 33% of the nominal 100%. It can easily be recognized that the light colour achieved at the end of the wake-up cycle is simply the light colour corresponding to 33% of the colour line. In other words, the light colour during steady state (horizontal portion of curve 2') differs from the light colour during steady state in the 100% situation (horizontal portion of curve 2).

The present invention aims to offer a solution to this problem.

According to an important aspect of the present invention, during the wake-up cycle, the colour of the output light is controlled independently of the momentaneous light intensity, such as to simulate the colour change of the rising sun, and such that the light colour obtained at the end of the wake-up cycle is fixed, independent of the steady state intensity. In a preferred embodiment, a user can also set this steady state colour.

Further advantageous elaborations are mentioned in the dependent claims.

The effect of the present invention is visualized in the right-hand diagram of FIG. 2, the left-hand and centre diagrams being identical to FIG. 1 for sake of comparison. Curve 1" is identical to curve 1': the light intensity gradually rises to 33% of the nominal 100%. Curve 2" is identical to curve 2: the colour path travelled by the colour point in colour space is identical to the colour path travelled in the nominal 100% situation.

It is noted that U.S. Pat. No. 7,280,439 discloses an illumination system that effects a colour change to simulate sunrise. However, this document does not disclose a user-adjustable maximum of the light intensity during steady state, nor does it disclose the consequences for the colour cycle.

US2004/0264193 discloses in general the controlling of a LED such as to control the colour temperature.

U.S. Pat. No. 5,327,331 discloses a wake-up lamp where the colour temperature is maintained constant while the light output intensity is increased.

BRIEF DESCRIPTION OF THE DRAWINGS

These and other aspects, features and advantages of the present invention will be further explained by the following description of one or more preferred embodiments with reference to the drawings, in which same reference numerals indicate same or similar parts, and in which.

DETAILED DESCRIPTION OF THE INVENTION

Figure 3:
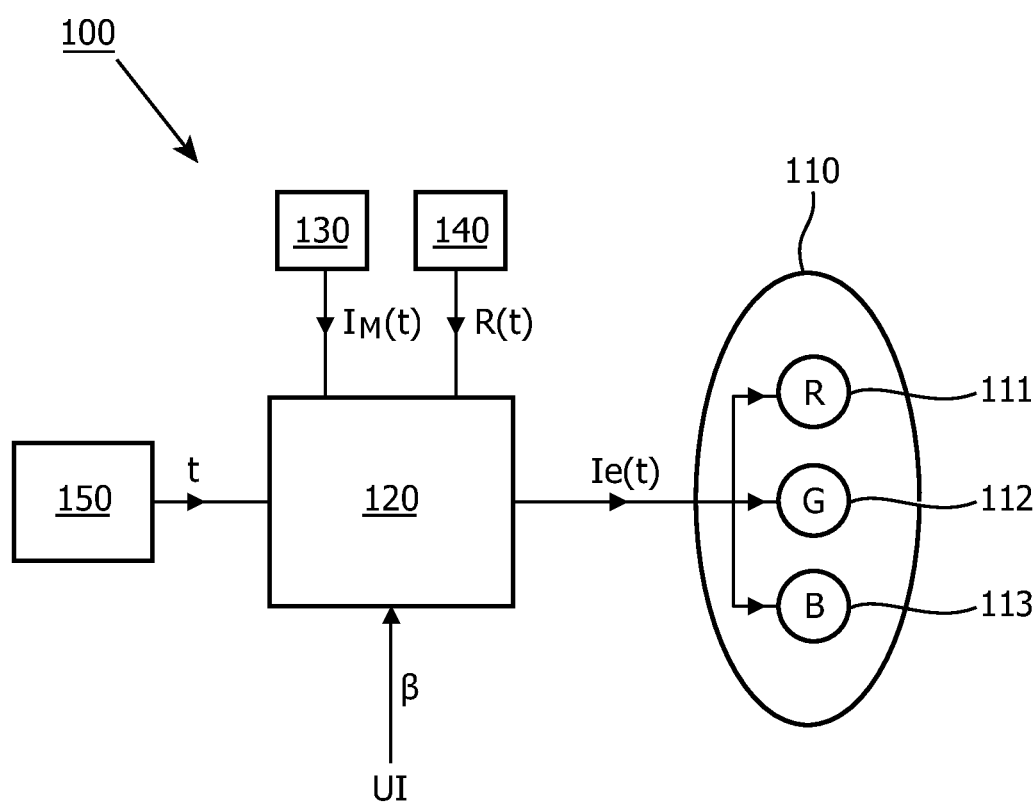
FIG. 3 is a block diagram schematically illustrating an exemplary embodiment of an illumination device according to the present invention.

FIG. 3 is a block diagram schematically illustrating a possible embodiment of an illumination device 100 according to the present invention. The illumination device 100 comprises at least one controllable light source 110, a control device 120 for controlling the light source 110, a first memory 130 associated with the control device 120, and a second memory 140 associated with the control device 120. The control device 120, which may for instance be implemented as a suitably programmed micro-controller, generates a control signal for the light source 110 such as to cause the light source 110 to generate light having a certain desired colour and a certain desired intensity.

By way of non-limiting example, the light source 110 comprises three (or more) LEDs (or other types of light generating elements) 111, 112, 113, each generating light having a distinct, ideally monochromatic, colour, and these colours being mutually different. For instance, these colours may be red (R), green (G), blue (B). As should be known to persons skilled in the art, the overall light output of the light source 110 is a mixture of these three light outputs, and the human eye perceives the overall light output mixture as having one mix colour, which mix colour depends on the mutual ratios of the three light contributions.

Although it should be known to persons skilled in the art, a brief summary of colour theory will be given below.

Colours can be represented by three mutually independent parameters; reference may be made to the CIE1931(XYZ) system, wherein X, Y, Z represent the intensities needed of light sources having particular defined colours, e.g. red 700 nm, green 546.1 nm, blue 435.8 nm, respectively, for obtaining a certain colour. Here, "colour" means a combination of chromaticity and brightness. In the CIE1931(XYZ) system, a change of one of the values of X, Y or Z will result in a combined change of chromaticity and brightness. A transformation can be made to a coordinate system where chromaticity and brightness are independent of each other. Such a system is for instance the CIE(xyY) system, having coordinates x, y, Y, wherein x and y are chromaticity coordinates and wherein capital Y indicates luminance. The transformation regarding the colour coordinates is defined by the following formulas:

$$x = \frac{X}{X+Y+Z} \tag{1a}$$

$$y = \frac{Y}{X+Y+Z} \tag{1b}$$

$$z = \frac{Z}{X+Y+Z} \tag{1c}$$

These formulas still show three variables x, y, z, but z is a redundant variable (i.e. not an independent variable) since z can be calculated from x and y according to $$z = 1 - x - y \tag{1d}$$

Figure 4:
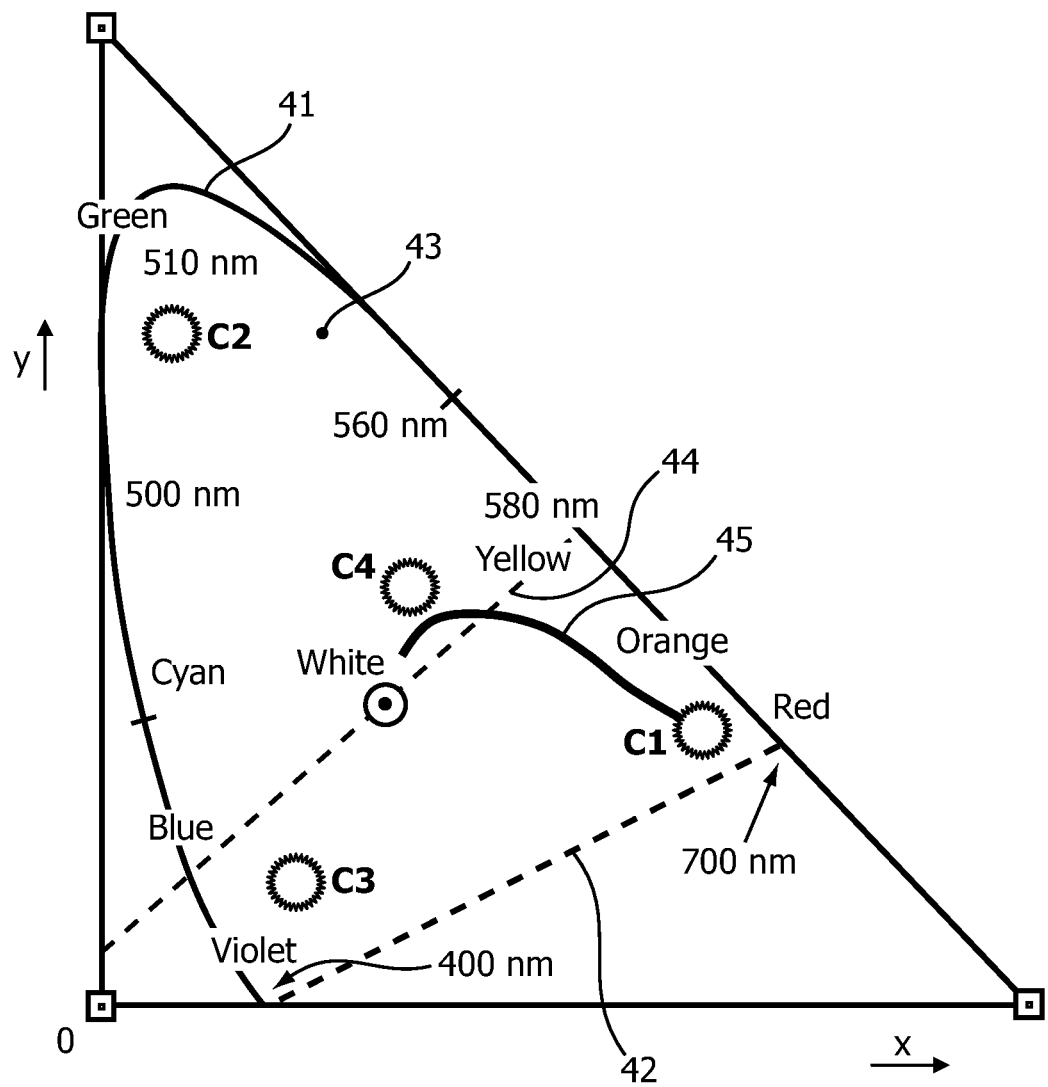
FIG. 4 schematically illustrates a colour diagram.

Thus, the chromaticity of all colours can be represented in a two-dimensional xy-plane, as shown in FIG. 4, which schematically shows a CIE(xy) chromaticity diagram. This diagram is well-known, therefore an explanation will be kept to a minimum. Points (1,0), (0,0), and (0,1) indicate ideal red, blue and green, respectively, which are virtual colours. The curved line 41 represents the pure spectral colours. Wavelengths are indicated in nanometers (nm). A dashed line 42 connects the ends of the curved line 41. The area 43 enclosed by the curved line 41 and dashed line 42 contains all visible colours; in contrast to the pure spectral colours of the curved line 41, the colours of the area 43 are mixed colours, which can be obtained by mixing two or more pure spectral colours. Conversely, each visible colour can be represented by coordinates in the chromaticity diagram; a point in the chromaticity diagram will be indicated as a "colour point".

Instead of "luminance Y", which indicates an absolute amount of light, for instance expressed in lumen, it is customary in the field of light sources to use "brightness B", which is a relative parameter. For each colour point (x,y), there is a maximum attainable luminance $Y_{MAX}(x,y)$. When the actual luminance Y has a value L, brightness is defined as $$B = L/Y_{MAX} \tag{2}$$

Thus, brightness is a value between 0 and 1.

Further, instead of colour coordinates x,y it is also possible to use hue and saturation. The basic concepts of Hue, Saturation and Brightness are most easily explained in the CIE 1931 (x,y) colour space, referring to FIG. 4, although in other colour spaces other definitions can be obtained. For simplicity, CIE 1931 (x,y) colour space is used in the following.

When two pure spectral colours are mixed, the colour point of the resulting mixed colour is located on a line connecting the colour points of the two pure colours, the exact location of the resulting colour point depending on the mixing ratio (intensity ratio). For instance, when violet and red are mixed, the colour point of the resulting mixed colour purple is located on the dashed line 42. Two colours are called "complementary colours" if they can mix to produce white light. For instance, FIG. 4 shows a line 44 connecting blue (480 nm) and yellow (580 nm), which line crosses a white point, indicating that a correct intensity ratio of blue light and yellow light will be perceived as white light. The same would apply for any other set of complementary colours: in the case of the corresponding correct intensity ratio, the light mixture will be perceived as white light. It is noted that the light mixture actually still contains two spectral contributions at different wavelengths.

It is noted that many visible colours can be obtained by mixing two complementary colours, but this does not apply for all colours, as can easily be seen from FIG. 4. Assume an assembly of three lamps producing three different colours with corresponding respective colour points C1 (close-to-red), C2 (close-to-green), C3 (close-to-blue): with such assembly, it is possible to produce light having any desired colour within the triangle defined by these three corresponding colour points C1, C2, C3.

In case a fourth lamp with colour point C4 (close-to-white) is added, colours are no longer obtained as a unique combination of three light outputs but can be obtained in several different ways as a combination of four light outputs. This may be especially useful if it is desirable to enhance a certain colour contribution, for instance yellow.

When the sun rises, its colour shifts from red via orange and yellow to white; on sunset, the opposite occurs. Curve 45 is an exemplary path, given only for sake of discussion, simulating the path travelled by the colour point of the sunlight. While the actual path travelled by the colour point of the sunlight, although it may vary depending on weather circumstances, can be considered as being a fixed fact, a practical path simulating or approximating the true path can be selected by a practitioner as desired. According to the present invention, the exact coordinates of the practical path are not relevant. What is relevant, according to the present invention, is that information defining such a practical path is stored in the first memory 130. This practical path will in the following be indicated as "sunrise approximation path".

The control device 120 is designed to operate in four possible modes, as follows.

In an OFF mode, the light source 110 is off.

In a STEADY mode, the control signal for the light source 110 is kept constant, so that the output light colour and output light intensity are constant.

In a WAKE-UP mode, the control device 120 changes its control signal for the light source 110 as a function of time, so that the output light colour point travels the sunrise approximation path from the red end to the white end, and so that the output light intensity is slowly increased.

In a FALL-ASLEEP mode, the control device 120 changes its control signal for the light source 110 as a function of time, so that the output light colour point travels the sunrise approximation path in the opposite direction, i.e. from the white end to the red end, and so that the output light intensity is slowly decreased. In a variation, the first memory 130 may store two different paths, a sunrise approximation path and a sunset approximation path, in which case the control device 120 makes the output light colour point travel the sunset approximation path in the FALL-ASLEEP mode. The "colour speed" may be constant or may vary as a function of time.

Normal use of the illumination device 100 will typically involve the sequence OFF/WAKE-UP/STEADY/OFF in the morning and OFF/STEADY/FALL-ASLEEP/OFF in the evening. The transition from OFF to WAKE-UP mode may be done automatically on the basis of a wake-up timer, but this is not shown in the drawing for sake of simplicity.

The control device 120 has a user input UI, via which the user can input user settings. One of the user settings may be the duration of the WAKE-UP mode and FALL-ASLEEP mode (these two not necessarily having the same duration). Once set, the duration of the WAKE-UP mode (or wake-up cycle time) may be considered to be a fixed value; for sake of explanation, it will be assumed that this value is equal to 30 minutes; the same applies to the duration of the FALL-ASLEEP mode.

Another user setting within the context of the present invention is the output light intensity during the STEADY mode, which will be indicated as steady state intensity $I_{STEADY}$. Preferably, the setting of the steady state intensity can also be varied during, for instance, the WAKE-UP mode, but in the following the steady state intensity will be considered to be a fixed value. The maximum intensity of the light source 110 possible in the STEADY mode will be indicated as $I_{MAX}$. The ratio $I_{STEADY}/I_{MAX}$ will be indicated as steady brightness $\beta$.

Figure 1:
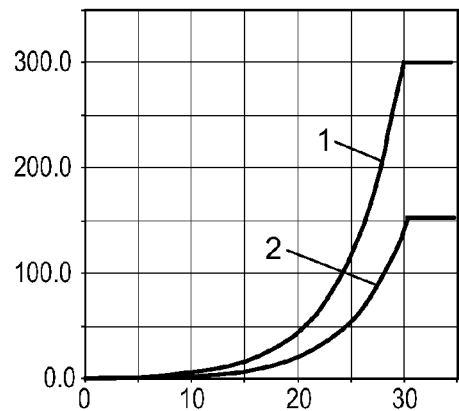
FIG. 1 shows diagrams of light intensity and light colour as a function of time for different situations.
Figure 1:
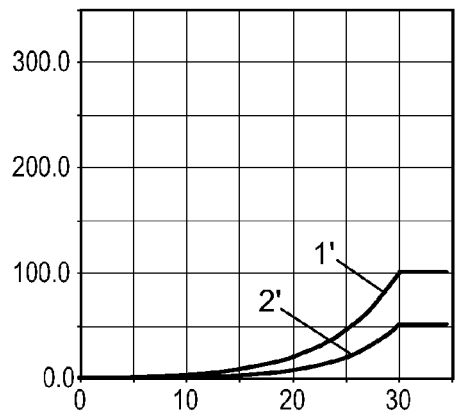
Figure 2:
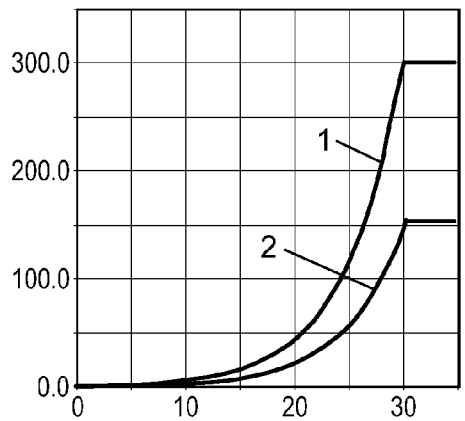
FIG. 2 shows diagrams of light intensity and light colour as a function of time to illustrate the present invention.
Figure 2:
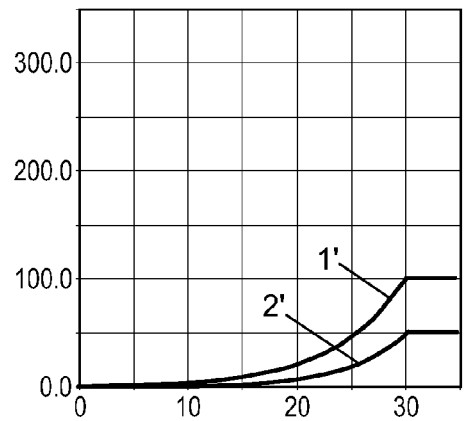
Figure 2:
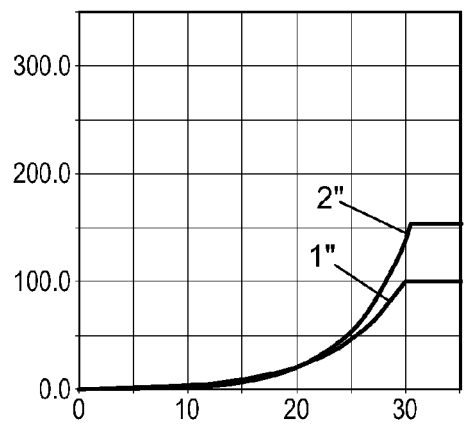

At all times during the WAKE-UP mode, the control device 120 will generate its control signal for the light source 110 on the basis of the information in the first and second memories 130, 140; the same applies to the FALL-ASLEEP mode. The control signal for the light source 110 in fact consists of individual control signals for individual LEDs 111, 112, 113 and possible additional white or yellow or amber LEDs. As mentioned before, the first memory 130 contains information to define the overall output colour as a function of time. This information may for instance be in the form of a look-up table, containing a fixed setting of the output current per time element for each light generating element, or for instance in the form of a formula, allowing the output current for each light generating element to be calculated as a function of time. Likewise, the second memory 140 contains information defining the development of intensity as a function of time; this intensity may be varied linearly with time, or parabolically (as shown in FIG. 2), or any other desired function.

For providing a time signal, the apparatus 100 comprises a clock device 150. Assume that the nominal duration of the WAKE-UP mode equals 30 minutes (1800 seconds), and that the control device 120 takes 100 steps: this means that the control device 120 will nominally consult the memories 130, 140 once every 18 seconds and adapts its output signals. Assume that the user has set a duration of $\alpha \cdot 30$ minutes ($\alpha$ being smaller than or larger than 1): this means that the control device 120 will practically consult the memories 130, 140 once every $\alpha \cdot 18$ seconds and adapt its output signals. Without giving a more elaborate explanation, it should be clear to a person skilled in the art how a time scale can be scaled in accordance with the duration set by the user. Further, it should be clear that the control device 120 may be designed to change its control signals in discrete steps, once every so-many seconds, but it is also possible that the control device 120 is designed to change its control signals continuously.

At all times t, the control device 120 calculates an individual intensity Ie(t) per light generating element 111, 112, 113 according to the following formula:

$$Ie(t) = IM(t) \cdot R(t) \cdot \beta$$

Here, IM(t) indicates the intensities that are calculated on the basis of the information in the first memory 130 alone. These intensities combine to the correct mixed output colour at the maximum intensity if R=1 and $\beta$=1. It is noted that IM is a function of time, thus implementing the change of colour as a function of time or, in other words, the travel along the colour path 45.

R(t) indicates the intensity ratio (between 0 and 1) as a function of time as derived from the second memory 140: this implements the desired time profile of the increase/decrease of intensity.

$\beta$ indicates the steady brightness as defined above: this implements the maximum setting instructed by the user.

It is noted that, since the intensities of all light generating elements are multiplied by the same factor $\beta \cdot R(t)$, the colour point of the mixed output light remains the same. It is further noted that varying intensities while maintaining the colour of individual light generating elements can be implemented by duty cycle control, as should be clear to a person skilled in the art.

Summarizing, the present invention provides an illumination device 100 with wake-up and/or fall-asleep functionality, comprising:

at least one controllable light source 110;

a control device 120 for controlling the light source 110.

In a STEADY mode, colour and intensity of the output light are maintained constant at a steady colour value and a steady intensity value.

In a WAKE-UP mode, the intensity of the output light is gradually increased from zero to the steady intensity value; in a FALL-ASLEEP mode, the intensity of the output light is gradually decreased from the steady intensity value to zero.

The control device 120 comprises a user input UI for receiving a user input signal defining the steady intensity value. The control device 120 generates a control signal for the controllable light source 110 such as to cause the colour of the output light to travel a predetermined path in a colour space, independent of the steady intensity value.

While the invention has been illustrated and described in detail in the drawings and foregoing description, it should be clear to a person skilled in the art that such illustration and description are to be considered illustrative or exemplary and not restrictive. The invention is not limited to the disclosed embodiments; rather, several variations and modifications are possible within the protective scope of the invention as defined in the appending claims.

For instance, in the embodiment as described above, two separate memories are provided, one defining the travel along the colour path as a function of time and the other defining the nominal intensity development as a function of time. It is also possible that one single memory contains the combined information IM(t)·R(t), defining colour and nominal intensity development as a function of time.

Further, in the embodiment as described above, the light source 110 comprises multiple light generating elements each having a fixed colour; in such a case, the present invention is implemented by varying the relative weight of the light output contributions of these elements. However, it is also possible to use one (or more) light generating elements, each capable of generating light of variable colour, of which the colour value is adjustable by the control device. The basis relevant issue is just that colour output and intensity of the light source 110, whether containing only one light generating element or two or more, can be controlled independently.

In the above embodiment, the control device 120 is described as specifically controlling the colour point of the output light to specifically simulate a sunlight effect. However, an embodiment does not need to be as sophisticated as that. For instance, it is possible that the light source 110 just comprises two light generating elements, one element generating white light and one element generating warmer light, wherein both light generating elements are controlled independently by the control device 120 such as to effect a colour shift independently of the STEADY intensity. The first light generating element may for instance be a CFL lamp and the second light generating element may for instance be a neon lamp (such as is used in night lamps or refrigerators).

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

In the above, the present invention has been explained with reference to block diagrams, which illustrate functional blocks of the device according to the present invention. It is to be understood that one or more of these functional blocks may be implemented in hardware, where the function of such a functional block is performed by individual hardware components, but it is also possible that one or more of these functional blocks are implemented in software, so that the function of such a functional block is performed by one or more program lines of a computer program or a programmable device such as a microprocessor, microcontroller, digital signal processor, etc.

The invention claimed is:

1. An illumination device with wake-up and fall-asleep functionality capable of outputting light with a gradually increasing or decreasing intensity, the device comprising:
   at least one controllable light source;
   a control device for controlling the at least one controllable light source;
      wherein the control device is capable of operating in a steady mode during which color and intensity of the output light are maintained constant at a steady color value and a steady intensity value, respectively;
      wherein the control device is capable of operating in one of: a wake-up mode during which the intensity of the output light is gradually increased from zero to the steady intensity value and a fall-asleep mode during which the intensity of the output light is gradually decreased from the steady intensity value to zero;
      wherein the control device comprises:
         a user input (UI) for receiving a user input signal defining a user defined steady intensity value; and
      wherein the at least one controllable light source is capable of producing output light of which the color value is variable independent of the output light intensity; and
         an overall intensity of the at least one controllable light source as a first function of time to reach the user defined steady intensity value at the end of the wake-up mode or to start with the user defined steady intensity value at the beginning of the fall-asleep mode;
         and vary a color value of the at least one controllable light source as a second function of time, wherein the color value achieving said steady color value is independent of said user defined steady intensity value.

2. The illumination device according to claim 1, wherein the at least one controllable light source comprises:
   at least two light generating elements of mutually different colors;
   wherein the control device varies the overall intensity of each of said at least two light generating elements combined in conformity with said first function of time and wherein the control device varies the intensity ratio of the at least two light generating elements in conformity with said second function of time.

3. The illumination device according to claim 1, wherein a duration of the wake-up mode and a duration of the fall-asleep mode is constant.

4. The illumination device according to claim 1, wherein the control device is capable of receiving a user input signal defining a duration of the wake-up mode and a duration of the fall-asleep mode.

5. The illumination device according to claim 1, further comprising a memory-containing information defining a color path to be travelled as a function of time.

6. The illumination device according to claim 5, wherein the control device is designed to calculate a color point on the basis of the information in the memory as a function of time, and to independently calculate the intensity as a function of time.

7. The illumination device according to claim 1, further comprising a memory containing information defining the intensity as a function of time.

8. The illumination device according to claim 1, wherein the control device is designed to generate a control signal for the at least one controllable light source to cause the color of the output light to travel a predetermined path in a color space independent of the steady intensity value.

* * * * *